(12) United States Patent
Wang et al.

(10) Patent No.: US 8,940,495 B2
(45) Date of Patent: Jan. 27, 2015

(54) RAPID AND SENSITIVE METHOD FOR QUANTITATIVE DETERMINATION OF THE LEVEL OF HEPARIN—PF4 COMPLEX INDUCED IMMUNOGLOBULIN ANTIBODIES

(75) Inventors: Xue-feng Wang, Chapel Hill, NC (US); Xuejie Wang, Chapel Hill, NC (US)

(73) Assignee: BioMedomics, Inc, Research Triangle Park, NC (US)

( * ) Notice: Subject to any disclaimer, the term of this patent is extended or adjusted under 35 U.S.C. 154(b) by 298 days.

(21) Appl. No.: 12/743,752

(22) PCT Filed: Feb. 26, 2009

(86) PCT No.: PCT/US2009/035222
§ 371 (c)(1),
(2), (4) Date: May 19, 2010

(87) PCT Pub. No.: WO2009/111254
PCT Pub. Date: Sep. 11, 2009

(65) Prior Publication Data
US 2010/0255510 A1    Oct. 7, 2010

Related U.S. Application Data

(60) Provisional application No. 61/067,756, filed on Feb. 29, 2008.

(51) Int. Cl.
G01N 33/53 (2006.01)
C12M 1/34 (2006.01)
G01N 33/86 (2006.01)

(52) U.S. Cl.
CPC .......... *G01N 33/86* (2013.01); *G01N 2333/522* (2013.01); *G01N 2400/40* (2013.01); *G01N 2800/222* (2013.01); *Y10S 435/97* (2013.01)
USPC .......... 435/7.25; 435/4; 435/287.2; 435/970; 436/501; 436/518

(58) Field of Classification Search
None
See application file for complete search history.

(56) References Cited

U.S. PATENT DOCUMENTS

| 5,972,718 | A | * | 10/1999 | Moghaddam et al. | ........ 436/506 |
|---|---|---|---|---|---|
| 6,394,952 | B1 | | 5/2002 | Anderson et al. | |
| 6,528,325 | B1 | | 3/2003 | Hubsher et al. | |
| 2002/0197697 | A1 | | 12/2002 | Abdelouahed et al. | |
| 2005/0261241 | A1 | | 11/2005 | Cardin | |
| 2006/0172438 | A1 | | 8/2006 | Milunic et al. | |
| 2006/0246513 | A1 | * | 11/2006 | Bohannon | ...................... 435/7.1 |
| 2007/0020768 | A1 | | 1/2007 | Rundstrom et al. | |

FOREIGN PATENT DOCUMENTS

| WO | WO 01/04159 | 1/2001 |
|---|---|---|
| WO | WO 01/16184 | 3/2001 |

OTHER PUBLICATIONS

The extended European Search Report issued Mar. 23, 2011 in the corresponding European Patent Application No. 09717826.3.*
David L. Carlberg, "Lateral-flow assays: Designing for automation," Published on IVD Technology (http://www.ivdtechnology.com) May 1, 1999.*
Tazzari, P.L., et al.,Transfusion Medicine, vol. 12: 193-198 (2002).
Woodhams, B.J. Thromb. Haemost., vol. 82: 157-158 (1999).
Suvana, S., et al., Blood, vol. 110, No. 13: 4253-4260 (2007).
Suh, J., et al., Blood, vol. 91, No. 3: 916-922 (1998).
510K Submission to FDA (I05359) "PF-4 Enhanced (Trademark)" for platelet factor 4 raidoimmunoassay, Genetic Testing Institute, Inc., 20925 Crossroads Circle, Waukesh, WI 53186, 2006.

* cited by examiner

*Primary Examiner* — Galina Yakovleva
(74) *Attorney, Agent, or Firm* — Charles T. Joyner

(57) ABSTRACT

Disclosed herein is a lateral flow immuno-assay system capable of rapidly, cost effectively, and quantitatively detecting and assessing the level of HIT antibodies in body fluids of a patient. Also taught are methods for employing the system to assist in diagnosis of HIT, and for screening or detecting a changing titer of HIT antibodies in the body fluids of a patient to determine susceptibility toward HIT.

18 Claims, 2 Drawing Sheets

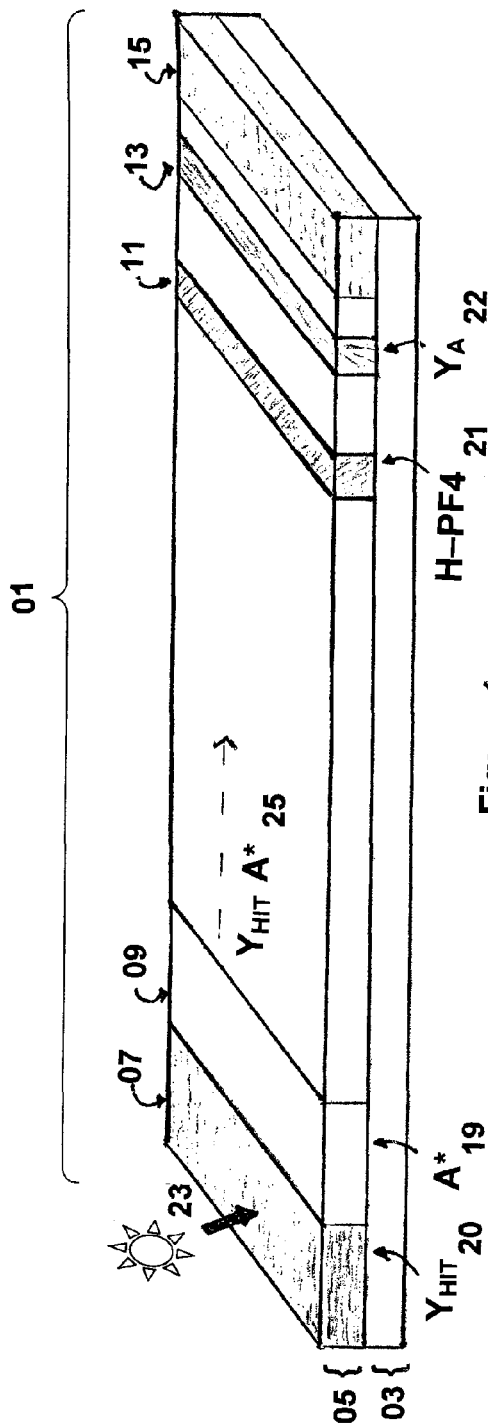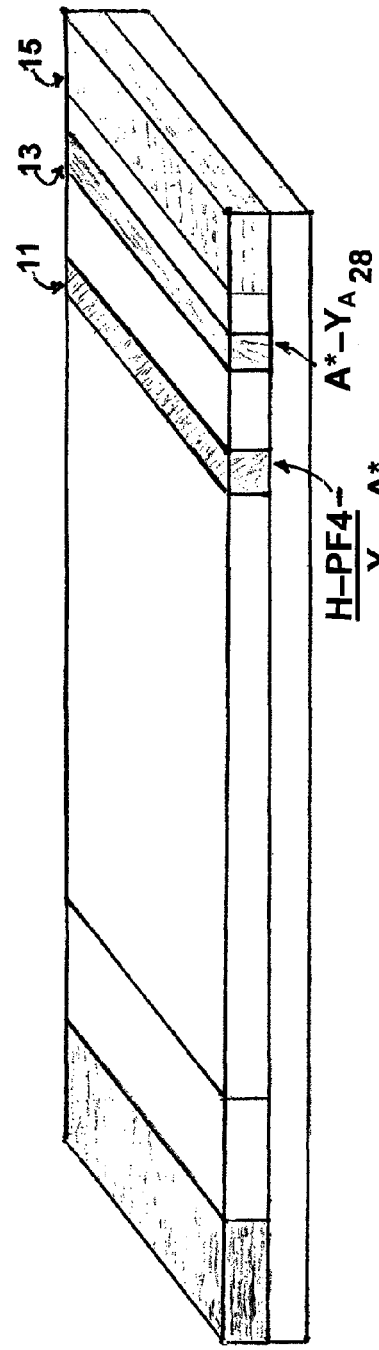
Figure 1
Figure 2

RAPID AND SENSITIVE METHOD FOR QUANTITATIVE DETERMINATION OF THE LEVEL OF HEPARIN—PF4 COMPLEX INDUCED IMMUNOGLOBULIN ANTIBODIES

This is a continuation-in-part of PCT application PCT/US2009/035222, under 35 USC §371, having the international filing date of Feb. 26, 2009, which claims the priority date, Feb. 29, 2008, filing date of the parent U.S. Provisional Application 61/067,756.

BACKGROUND OF THE INVENTION

An animal's immune system provides a stream of protein molecules know as antibodies that circulate through the animal's blood stream. When large toxin molecules or microorganisms, known as antigens, enter the blood stream, the immune system, through a complex biochemical sequence, recognizes that the antigens are foreign to the animal's system, and hence, a threat. In response to the invasion of antigens, the immune system rapidly produces "customized" antibodies that attach themselves to the specific site on the antigen. The attached antibodies act as markers to identify the antigens or other material produced by the immune system, which in turn destroy the antigens.

Because antibodies are extremely specific; selective; and sensitive, and relatively easy to generate, scientists have recognized that they can be the basis for a variety of useful tests known as immunoassays. In its basic form, an immunoassay for a specific antigen involves allowing a test sample of material of unknown composition, an analyte, to come in contact with immobilized antibodies that bind to the specific antigen. If the antigen is present, it will bind, i.e. conjugate, with the antibodies and also become immobilized. The immobilized antibodies are washed to remove any free analyte, and then treated with labeled antibodies that bind to a different site on the antigen than the immobilized antibodies. If the antigen in question was present in the analyte, it will now be conjugated to the labeled antibodies and also to the immobilized antibodies. Presence of the antigen can be detected by sensing the label.

Typically, labels have distinct signatures detectable by electromagnetic radiation absorption, emission, or both. A particularly useful technique is to use labels that are florescent. That is, they absorb electromagnetic radiation above the frequency range of visible light then instantly emit visible light. The strength of the absorption or emission can be directly correlated to the amount of label, and hence the antibody being observed. Alternatively, a label detectable by electronic means may be used. For example, the label may impede a radio frequency signal and the amount of impedance detected by electronic means.

Thus, Immunoassays are tests that take advantage of the specific binding of an antibody to its antigen and are discussed and illustrated in most University level biochemistry textbooks. For example, see L. Nelson, et al. *Lehninger Principles of Biochemistry*, 3$^{rd}$ Ed., 231-233, Worth, N.Y. (2000) and L. Stryer, *Biochemistry*, 4$^{th}$ Ed., 60-63, W.H. Freeman, NY (1995). The main characteristic of immunological techniques is the appropriate labeling of the antibody or the antigen. This label helps create a signal that correlates with the immunoreaction and allows the detection of the analyte of interest. In laboratory assays, various wash steps are required to remove free labeled or unlabeled reactants and allow the detection of the analyte by the bound and labeled reactants. Test results may be quantified by comparison to a calibration curve established by a previously run series of assays using known amounts of analyte.

A widely practiced form of immunoassay is the enzyme-linked immunosorbent assay (ELISA); supra, Nelson, et al., and Stryer. There are many variations of ELISA's, most of which require multiple steps and a moderate to extensive skill level to execute. However, one category of immunoassay, i.e. the well-known lateral flow immunoassay (LFIA), of which home pregnancy tests are an example, are simple, typically requiring only one step, and requiring no technical sophistication to perform. Thus, LFIA can be easily performed by non-trained users and used on-site during sample collection. The simplicity of the tests paired with their quick return of results (2-15 minutes), means that testing is cost-effective. LFIA represent an appropriate point-of-care (POC) and field-use technology that can be applied to a broad range of applications. Despite the advantages of LFIA, they are often limited to simple screening applications. This is because LFIA's, in their present form, are not easily quantifiable and are not sensitive enough for certain applications.

Each year millions of patients, about a third of those hospitalized, are exposed to heparin. About 1% to 5% of these heparin-exposed patients develop a severe complication known as heparin-induced thrombocytopenia often referred to as "HIT". Venous or arterial thrombosis is among the effects of HIT, and in patients suffering from acute thrombosis, HIT may be fatal. After discontinuation of heparin in patients with HIT, the platelet levels generally return to normal. Therefore, timely and accurate diagnosis of HIT can alleviate pain and even prevent death. See Arapally et al, *N Engl J Med*, 355; 8: 809.

The immunoglobulin antibodies, such as IgG, IgA, IgE, or IgM antibodies, that develop after five or more days of heparin therapy appear to cause HIT. These antibodies differ from those associated with other forms of drug-induced thrombocytopenia in that, in the presence of optimal concentrations of heparin, they activate blood platelets. This activation causes the platelets to release the contents of their storage granules and to undergo membrane changes that create sites for the binding of a coagulation factor, fibrinogen, normally present in plasma (B. H. Chong, et al., *Br. J. Haematol.*, 64: 347 (1986)). Heparin first binds to platelet factor 4 (PF4), which arises during heparin treatment, to form a highly immunogenic complex on the surface of platelets. Next, in susceptible patients, immunoglobulin, e.g. IgG, IgA, IgE, or IgM antibodies to the antigenic heparin-PF4 complex develop that bind with the complex to activate platelets via Fc receptors on the surface of the platelets (M. F. Cooney, *Critical Care Nurse*, 26, 6: 30 (2006).

Several HIT diagnostic procedures and assays are reported in the art, but each has drawbacks that limits its use in accurately, rapidly, reliably, and cost effectively diagnosing the risk of HIT. For example, U.S. Pat. No. 5,972,718 teaches an ELISA type immunoassay. However, while ELISA procedures and assays are suited for laboratory environments, they are not well suited for POC use because of their complexity and the requirement for skilled operators. In practice, an ELISA requires 3-4 hours of skilled technician time and typically involves turnaround times of one day to one week.

SUMMARY OF THE INVENTION

There is a need for a sensitive, accurate, reliable, quantitative, cost effective, rapid, and easy to use assay for point of care application to assist in the diagnosis of HIT, and the invention described herein fulfills that need in all its aspects.

The present HIT immuno-flow type assay in its various forms includes, but is not limited to, lateral flow immuno-assays and flow-through assays.

A first aspect is a method wherein the level of heparin-PF4 complex induced immunoglobulin antibodies in a patient is determined by direct measurement with a point-of-care immuno-flow assay system, in particular, a lateral-flow immunoassay system. A first embodiment of the first aspect is a method of quantitatively determining a body fluid level, e.g. blood, or component thereof, of heparin-PF4 complex induced immunoglobulin, e.g., IgG, IgA, IgE, or IgM antibodies by a point-of-care lateral-flow immunoassay system. A second embodiment of the first aspect is a method for detecting a changing titer of heparin-PF4 complex induced immunoglobulin antibodies in a patient by multiple applications over time of the first embodiment.

A second aspect of the invention is a point-of-care immuno-flow assay system, in particular, a lateral-flow immunoassay, for quantitatively measuring, directly or indirectly, heparin-PF4 complex induced immunoglobulin antibodies level in a patient. A first embodiment of this aspect is an immuno-flow assay system for directly determining body fluid, e.g. blood, or component thereof, level of heparin-PF4 complex induced immunoglobulin antibodies in a patient. A second embodiment is a point-of-care lateral-flow immunoassay system for quantitatively determining, directly or indirectly, in a body fluid, e.g. blood, or component thereof, level of heparin-PF4 complex induced immunoglobulin antibodies in the patient.

BRIEF DESCRIPTION OF THE DRAWINGS

FIG. 1 schematically depicts the elements assay strip of the lateral-flow immunoassay system of the invention.

FIG. 2 schematically depicts the assay strip of the invention at the completion of the assay.

DETAILED DESCRIPTION OF THE INVENTION

Figure 3:
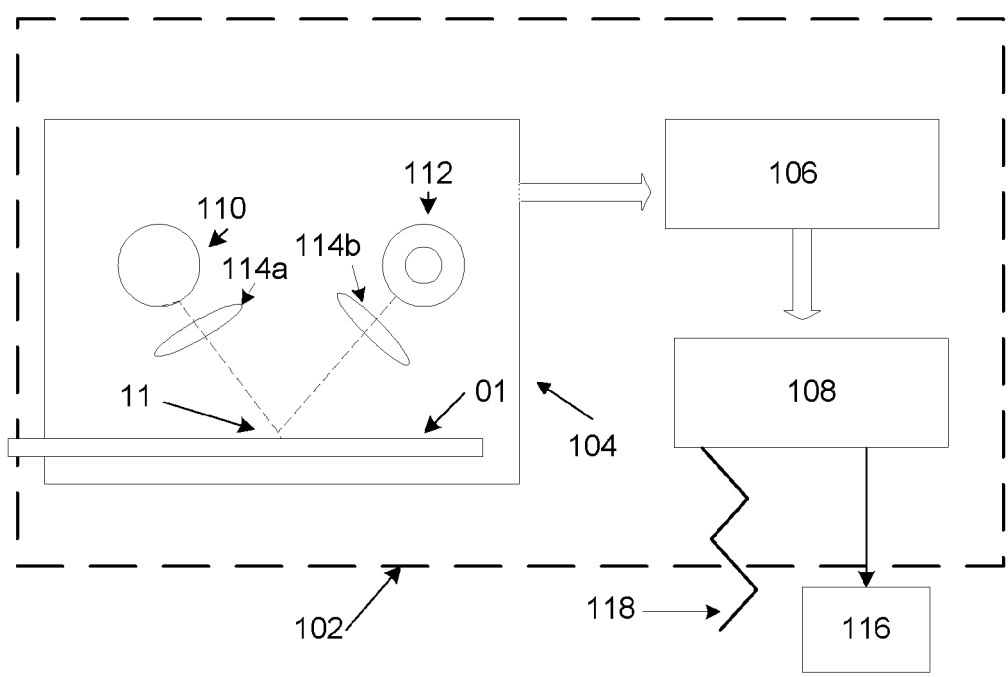
FIG. 3 schematically depicts a lateral-flow immunoassay system reader with associated equipment.

LFIA's are widely known in the scientific and patent literature relating to diagnostic assays. See, David Carlberg, "Lateral-flow Assays: Designing for Automation," *IVD Technology*, (Cover Story) May 1999. Compared with other immunoassay formats such as ELISA's, the major advantages of LFIA's are their ease of use, because aside from the dispensing of the sample, no additional sample or reagent handling steps are usually necessary. In a lateral-flow assay system, antibody-antigen reactions, as well as the removal of excess reactants, takes place by chromatographic separation driven by capillary forces. The detector reagent (i.e., the labeled antibody) and the sample wick through the pads or membranes of the test strip. At a capture line, i.e. test line, the detector reagent interacts with the capture reagent, which has been immobilized on the membrane. The test result is then evaluated visually, typically by two lines—a test line and a reference line.

When a patient is being treated with heparin, e.g. as part of a surgical procedure, the assay system of the present invention is a convenient means of monitoring the patient's blood, or other body fluid, level of heparin-PF4 complex induced immunoglobulin antibodies to determine if the patient has HIT or is susceptible to HIT. The LFIA and associated device taught herein, because of simplicity, robustness, and rapid completion time are well suited for point of care clinical use.

As used herein, the term "point of care" (POC) refers to a medical diagnostic procedure (as well as the means for its executing) that is particularly adapted for use in the immediate vicinity of the patient being treated. For example, during a surgical procedure, the present invention may be conveniently employed within the operating room in order to fully capitalize on its ease of use and rapid turn-around time. However, the skilled artisan will appreciate that the POC assay of the present invention may also be used to advantage in a wide variety of other settings. For example, it may be used in large central clinical laboratories and well as small physician office and community hospital laboratories. Further, it is well suited for military medicine in a field environment.

Relative to other immunoassays for antibodies which indicate possible onset of HIT, the present invention uniquely combines the attributes of fast turnaround (<30 minutes), quantitative capability, high sensitivity, and cost effectiveness. The combination of these benefits makes practical the new applications of: 1) pre-screening patients for HIT antibodies prior to administering heparin in the current clinical setting and 2) tracking a changing titer of HIT antibodies Pre-screening is generally not done with today's slow turnaround and costly tests. However, patients may carry antibodies from heparin exposure in previous hospital stays; their records and/or personal memory or knowledge may not record such exposure. The time to onset of thrombocytopenia after the initiation of heparin in patients with no previous heparin exposure or remote exposure (more than 100 days) normally occurs 5-10 days after heparin exposure, and thus the ELISA test is normally five days after heparin exposure. However, thrombocytopenia it may occur in hours in a patient with a history of recent (last 100 days) exposure to Heparin from a previous hospital stay (Arapally et al, N ENGL J MED 355; 8:809). The rapid, cost effective, quantitative POC assay of the present invention may be used for pre-screening patients to avoid HIT by reliably informing the attending physician of the level of circulating HIT antibodies. That is, the attending physician may choose not to prescribe heparin if the HIT antibody level is above a certain point.

As a cost effective and rapid turnaround, yet quantitative, POC test, the assay system of the invention can be employed as a daily or more frequent series, to inform physicians of a changing concentration of HIT antibodies which are approaching but have not reached the numeric (optical density) value considered to be a HIT "positive" test. Physicians would be enabled to take appropriate corrective action, e.g. switching to alternative anticoagulants, prior to a positive test confirming HIT onset. Moreover, the rate of change discernable from multiple rapid turnaround tests is informative and similarly actionable information for physicians. Finally, the rapid, quantitative and low cost test series could enable physicians to track the rising titer prior to or concurrent with observation of clinical indications of HIT rather than following such observation, as is the current clinical practice (Vide supra, Arapelly et al, 813, regarding current clinical practice), again potentially enabling earlier corrective action.

The skilled artisan will appreciate that a quantitative assay may also be used as a qualitative or semi-quantitative assay. The present invention may be used in a qualitative mode to answer the simple question, "Are any HIT antibodies detected in the sample?" with a simple, positive or negative answer. Likewise, if any HIT antibodies are detected, the present invention can return a semi-quantitative response such as "a small amount, a moderate amount, a large amount, or an extremely large amount. There may be occasions when less than a full quantitative reading will suffice.

For the following description of the invention, readers will find it convenient to have FIGS. 1-3 before them.

FIG. 1 is a schematic depiction of the assay strip LFIA 01 of lateral-flow immunoassay system of the present invention. LFIA 01 comprises a rigid or semi-rigid backing 03, e.g. plastic or glass, which supports membrane layer 05, that is an inert, fibrous material capable of supporting movement of liquids by capillary action, and under certain conditions, binding biologically derived molecules such as proteins or antibodies. An example of such a fibrous material is nitrocellulose, which is widely used as LFIA membrane material. Optionally, membrane layer 05 may be comprised of one or more layers that may be of the same or different compositions. In the art of lateral-flow immunoassay systems, a strip of membrane, e.g. membrane layer 05, on a plastic support is often referred to as a "card" and membrane cards of various compositions are commercially available.

Membrane layer 05 is zoned into functional areas referred to herein as sample pad 07, conjugate zone 09, test line 11, reference line 13, and wicking pad 15 arrayed in the order shown in FIGS. 1 and 2. Conjugate zone 09 and test line 11, test line 11 and reference line 13, and reference line 13 and wicking pad 15 are separated by flow zones. Optionally, sample pad 07 may be enhanced with features that promote the efficiency and accuracy of binding in LFIA 01. For example, sample pad 07 may be fitted with a blood preparation means so that whole blood may be converted to a form more amenable for LFIA analysis such as serum. If a body fluid other than blood is the sample, analogous preparation means may be employed to make that fluid amenable for LFIA analysis. Additionally, sample pad 07 may be supplied with preserving, stabilizing, flow promoting, and buffering agents. Sample pad 07 may be layered on top of membrane layer 05 or may be integrated into this membrane.

Conjugate zone 09 contains a means for labeling HIT antibodies that may be present in the sample for which LFIA 01 is intended to assay, so that the labeled antibodies can be detected optically or electronically at the conclusion of the assay. Conjugate zone 09 is supplied with labeled molecules of an antibody binding ligand, such as recombinant protein A affixed with a label, "labeled protein A 19" (shown symbolically in FIGS. 1 and 2 as "A*"). The label is detectable by emission or absorption of electromagnetic radiation, electronic means, other means employed in the immuno-assay art, such as enzyme labeling and substrate development. Suitable labels include materials that fluoresce, phosphoresce, or otherwise emit or absorb radiation. Conveniently, intensely colored, e.g. nano scale latex or gold, particles are useful as labels in the present invention. Optionally, conjugate zone 09 may be integrated into sample pad 07.

Test line 11 and reference line 13 are zones delineated on the fibrous material that comprises membrane layer 05. Immobilized on the strip of membrane layer 05 that forms test line 11 is capturing complex 21 (vide infra for discussion) capable of reacting with the immunoglobulin HIT antibodies 20 that may be present in the sample of body fluid, such as blood, or a component thereof, subjected to assay using LFIA 01. The immunoglobulin HIT antibodies 20 (represented in FIG. 1 as "$Y_{HIT}$") may be typically IgG, IgA, IgE, or IgM induced by heparin-PF4 complexes in the body of a patient.

Capture complex 21 may be a heparin-PF4 complex (as illustrated in FIGS. 1 and 2) or another PF4 complex that has a strong propensity to bind with immunoglobulin HIT antibodies 20. Studies suggest that when PF4 complexes with heparin, the configuration of PF4 is contorted to enhance the antigencity of PF4. See for example, Suh, et al., *Blood*, vol 91, No, 3, pp 916-922 (1998) and Suvarna, et al., *Blood*, Vol 110, No. 13, pp 4253-4260 (2007). Other agents have been found that mimic heparin's influence on the configuration of PF4. For example, polyvinyl sulfonate (PVS) has been used to generated a complex with PF4 that binds to immunoglobulin HIT antibodies 20 in a manner comparable to that of a heparin-PF4 complex. Likewise, other molecules such as proteins, peptides, or heparin-like moieties can be selected or engineered to bind with PF4 to yield complexes that to equal or exceed the immunoglobulin HIT antibody capturing potential of a heparin-PF4 complex. It is also possible that PF4 mimics might be employed in lieu of true PF4. Thus, all complexes capable of binding to immunoglobulin HIT antibodies 20 are within the scope of the present invention for use as capture complex 21.

Immobilized on the strip of membrane layer 05 that forms reference line 13 is a second antibody binding ligand capable of reacting with antibody binding ligand in conjugate zone 09 (as noted above, "labeled protein A 19)." Thus, reference line 13 is comprised of a) antibodies that bind to protein A, b) antibodies that recognize antibodies bound to the labeled protein A, or c) a ligand that binds directly or indirectly the label and are designated collectively herein as "binding reagent A 22." In FIG. 1, label binding reagent A 22 is noted as "$Y_A$".

The assay using LFIA 01 is initiated by placing onto sample pad 07 (indicated in FIG. 1 by the heavy arrow) a sample, typically a drop, of body fluid, such as blood, or a component thereof, e.g. plasma and serum, hereinafter "sample 23", suspected of containing immunoglobulin HIT antibodies 20. As the liquid components of sample 23 flow by capillary action into the region of conjugate zone 09, immunoglobulin HIT antibodies 20 contained in the sample conjugatively bind to the molecules of labeled protein A 19 to form antibody complexes 25 (shown symbolically in FIG. 1 as "$Y_{HIT}A^*$"). That is, antibody complexes 25 are comprised of immunoglobulin HIT antibodies 20 bound to molecules of labeled protein A 19. Antibody complexes 25 move out of conjugate zone 09 by capillary action through membrane 05 and advance toward test line 11 (schematically illustrated in FIG. 1 by a dashed arrow).

In FIG. 2, complexes 25 have migrated to test line 11, where they become bound to units of capture complex 21 (illustrated in FIGS. 1 and 2 as a heparin-PF4 complex) and are trapped as antibody complexes 27 at test line 11. In FIG. 2, antibody complex 27 is symbolically represented as "$H-PF4-Y_{HIT}A^*$". Thus, at test line 11 complex 27 may detected by the visualization of labels that were part of antibody complexes 25.

Those molecules of labeled protein A 19 that do not bind to test line 11 continue to move through membrane layer 05 to the reference line 13. As noted above, Immobilized at reference line 13 are ligands that can directly or indirectly bind the label 22 that are capable of binding to molecules of a labeled protein A 19 to form complex 28 shown as "$A^*-Y_A$" in FIG. 2. Therefore, labeled protein A 19 that not conjugated to immunoglobulin HIT antibodies 20 in sample 23 to form antibody complexes 25, and hence, immobilized at test line 11, are now immobilized at reference line 13 in complexes 28.

Absorption or emission of electromagnetic radiation or enzymatic detection at reference line 13 indicates that the test has been completed and is valid. For example, appearance of the label affixed to labeled protein A 19 at reference line 13 and also appearance of the label at test line 11 indicates that the test is complete and there is some immunoglobulin HIT antibodies 20 in the sample. Conversely, no appearance of the label at test line 11, but appearance at reference line 13, indicates the there is no immunoglobulin HIT antibodies 20 in the sample or the amount is below the sensitivity of the assay. No appearance of the label at either test line 11 or reference line 13 indicates either the assay is not complete or it is faulty in some manner and should be repeated. Thus, reference line 13 is a "control line" in immunoassay terminology. Any materials not immobilized at test line 11 or at reference line 13 continue to move through membrane layer 05 and are absorbed into wicking pad 15. At this point, the assay is fully developed and may be analyzed.

Conveniently, LFIA 01 may be housed in a cassette that protects it and facilitates its handling and analysis. Such protective cassette, usually constructed of a polymeric material, are provided as an integral part most commercially available LFIA units, and the utility of a protective cassette is widely taught in the technical and patent literature. Typically, a LFIA protective cassette provides at least one port for introducing a sample to be assayed and one or more windows for viewing and reading test and reference lines. For example, see David Carlberg, "Lateral-flow Assays: Designing for Automation," *IVD Technology*, (Cover Story) May 1999. A LFIA protective cassette may also be configured to facilitate proper orientation in an electro-optical reader. Further, a LFIA protective cassette may be imprinted with useful indicia, such as directions for use, warnings, and bar codes for identification.

A series of samples having identical volume with varying, but known, amounts immunoglobulin HIT antibodies 20 are assayed using the LFIA 01 described above. A curve or standardized chart defining the relationship of the amount of immunoglobulin HIT antibodies 20, present in the samples and the level of absorption or radiation detected at the test line is established. The result of an assay of a sample having an unknown amount of immunoglobulin HIT antibodies 20 is compared with the standardized chart to determine the amount of analyte in the sample thereby enabling the LFIA of the present invention to quantitatively determine the level of immunoglobulin antibodies in a sample of a given volume.

FIG. 3 schematically depicts a means for reading, i.e. analyzing, the developed assay. The developed assay may be read by visual comparison of the density of the test line with a standardization chart described above. However, reading by an electro-optical device schematically illustrated in FIG. 3 and described below is much preferred because of the greater sensitivity and consistency offered by such devices. Further, such electro-optical devices may be configured to yield a digital output that may serve as an input to other computer systems for long term storage and extensive data analysis.

Turning to FIG. 3, electro-optical reader 102 is comprised of electro-optical sensor 104 in communication with electronic signal processor 106, which in turn is optionally in communication with interpretation means 108. A developed LFIA 01 (described above and illustrated in FIGS. 1-2) is inserted into electro-optical sensor 104 of reader 102 where a source of electromagnetic radiation, typically light source 110, illuminates the test line 11 (FIGS. 1-2) of LFIA 01. Typically, LFIA 01 will be housed in a protective cassette, which assists in optimally orienting the LFIA 01 within electro-optical sensor 104. Light source 110 may be an emitter of IR, visible, or UV light. Light absorbed by the test line 11 is directly proportional to the density of the test line, and thus, proportional to the amount of the immunoglobulin antibodies (show as 20 in FIG. 1) that were present in the test sample (23 in FIG. 1). Therefore, the light reflected from the test line 11 is indirectly proportional to the light absorbed. That is, the more light absorbed by test line 11, the less light is reflected.

To receive electromagnetic radiation reflected from test line 11 is an electromagnetic radiation detector 112. If the electromagnetic radiation is light, e.g. IR, visible, or UV, the detector 112 might be a photo cell, camera, CCD line scanner, or other light sensing devise position to sense light reflected from test line 11. Detector 112 may be comprised of a single or multiple units, and it includes any associated electronic circuitry such as power supplies, amplifiers, and data processing units. Conveniently, lens 114a focuses light onto test line 11 while lens 114b focuses the light reflected from test line 11 onto detector 112. In cases where the detection mode is fluorescence, detector 112 receives light that fluoresces from test line 11 rather than reflected light. Further, in the fluorescence mode, the light illuminating test line 11 may be in the visible or UV range.

Detector 112 is in communication with signal processor 106. For example, detector 112 generates an electric voltage proportional to the light it senses, and that voltage is transmitted by a suitable means such as shielded cable to signal processor 106. Signal processor 106 converts the voltage, i.e. the signal, received from detector 112 into a form that can be perceived by human senses. Typically, signal processor 106 displays the signal from detector 112 in a visual analog or digital form, e.g. a meter, digital numerical readout, or printer.

The display from signal processor 106 may be read directly by a human operator and compared with a previously prepared calibration chart (described above) to determine the amount of immunoglobulin antibodies 20 in the sample of blood. Optionally, signal processor 106 may be in communication with interpretation means 108, which is a data processing means, e.g. a computer, that may be programmed to automate the process of reading the output from signal processor 106 and comparing that reading with a calibration chart to determine the level of immunoglobulin antibodies 20.

Interpretation means 108 may be programmed to signal the health care providers by visual and/or audio means 116 that there is a rising titer of immunoglobulin antibodies 20. Interpretation means 108 can store results of multiple tests over time, which is a useful data base for both patient care and medical research. Further, as a particular advantage, when the results are recorded in digital form, such result can be sent by electronic means 118 in "real time" via, phone or internet, directly to consulting health care providers even if they are at remote locations.

Any means known in the art for detecting labels on antibodies such as detection of electromagnetic absorption, emission, or both; or detection by electronic means may be used in the invention. For example, labels that absorb visible light may be visualized directly by eye or indirectly by an electro-optical device are frequently employed as are labels that are fluorescent under UV light or visible light. In some applications, phosphorescent labels may be employed.

Biosensors are devices that detect an analyte that combines a biological component (e.g. tissue, enzymes, antibodies, and nucleic acids) with a physicochemical element (e.g. optical or piezoelectric) in association with electronic circuitry. Biosensors can be related to nanotechnology such as nanotube based sensing. Herein biosensors and associated components are collectively referred to as "electronic means of analyte detection."

In addition to determining the level of heparin-PF4 complex induced immunoglobulin antibodies the assay of the present invention may be configured to concurrently quantitatively detect one or more other bio-markers in the body fluid of a patient. Examples of such bio-markers include, but are not limited to antibodies, DNA, proteins, toxins, and complex factors. For example, the assay may be configured to concurrently detect level of D-dimer.

Preparation and employment of the invention will be further understood from the following non-limiting examples.

The reader will find it helpful to refer to FIGS. 1-3 as well as the corresponding description of those figures presented above.

EXAMPLES

Summary

A mixture of modified PF4 is incubated with heparin to form a PF4 heparin complex, hereafter referred to as the "Complex," which is striped onto a supported nitrocellulose membrane such as membrane 05 where it binds to form a test line, such as test line 11. A clinical sample of a body fluid, such as blood, or a component thereof, is applied to a sample pad, e.g. sample pad 07, comprising reaction conditioning reagents. Antibodies within the sample are labeled by the rehydration of recombinant protein A affixed to colored latex particles also contained on the sample pad or in a separate conjugation pad zone, e.g., conjugation zone 09. The labeled sample migrates across the nitrocellulose membrane. If the sample contains anti-complex antibodies, these antibodies bind to the complex and a measurable signal is produced in proportion to the concentration of antibodies specific for the complex. Antibodies not captured at the test line are subsequently captured by molecules of protein A at the reference line, e.g. reference line 13, or they migrate and onto an absorbent pad material, e.g. wicking pad 15.

Example 1

Preparation of the Complex

Heparin (HP), 40 ul of 1000 U/mL, in phosphate buffered saline (PBS, Fisher Scientific PN: BP665-1) is mixed with 94 ul of PF4 (1.4 mg/mL, HPF, BioMedomics) and 56 ul of water, then incubated at room temperature for 30 minutes to yield the Complex mixture. The Complex mixture is then mixed with stabilizing agents by adding 4 ul of 50% sucrose (Fisher PN: S5) with 4 ul of 25% trehalose (Sigma PN: T9449) and 2 ul of 1M TAPS buffer (Sigma PN: T5441, pH 9.0).

Example 2

Preparation of the Membrane

The Complex mixture described above is striped onto a Millipore Hi-Flow mylar backed nitrocellulose membrane (25 mm wide, SHF0900425) affixed to an adhesive backed card (polystyrene 59 mm by 305 mm from GML or equivalent) at 0.075 ul/mm using an Imagene Isoflow striper (or equivalent) at 45 mm/second under conditions described by the manufacturer's user manual to create a test line, The test line is proximal to the sample pad at a position to be determined by the cassette holder assembly and, if employed, corresponding position for a reader. Simultaneously, a reference reagent comprising of 0.25 mg/mL of recombinant protein A (Repligen PN: rPA-50) is mixed with 1% sucrose/0.5% trehalose/10 mM TAPS pH 9.0 (as was done with the Complex mixture) and striped at 0.075 ul/mm at 45 mm/second at the same time as the Complex, but at a position upstream of the test line as designated by the reader and/or cassette holder assembly to create a reference line. The striped membrane is then baked at 56° C. for one week.

Example 3

Preparation of the Protein A Latex Particles

Dark blue carboxy-latex particles, "beads," (Bangs Beads, DC02B, 0.33 micron or equivalent), 10% in 100 ul, are covalently coupled by washing the beads with 50 mM MES (Sigma PN: M3885) pH 4.5, adding 1 mL of a fresh preparation of 10 mg/mL EDAC (Sigma PN: E1769) in 50 mM MES, pH 4.5, incubating for 30 minutes at room temperature. The resulting material is pelleted in a centrifuge at 13.4K×g for 5 minutes, the pellets washed with 50 mM MES pH 4.5, re-suspend (with sonication in water bath using Branson desktop sonicator) with 1 ml of 0.65 mg/mL recombinant protein A in 1×PBS, vortex, sonicate, and, finally, incubated at RT overnight. Next, 100 ul of 10% BSA (Proliant Biologicals PN: 68100 or equivalent)/100×TE (Fisher PN: BP1338), is vortex sonicated, and incubated at RT for at least 1 hour. The beads are centrifuged to form pellets, which are washed with 1 mL PBS. The wash step is repeated three times to remove unbound protein A and excess blocker ingredients. After re-suspending the recombinant protein A (rPA) beads in 1 mL of 4% sucrose/0.05% sodium azide (Sigma), they are stored under refrigeration until needed.

Example 4

Preparation of Sample Pad

A glass fiber pad (Ahlstrom 8964 or equivalent) is saturated with a mixture of 1% ethylenediamine tetrakis(propoxylate-block-ethoxylate) tetrol (Sigma PN: 4335539) surfactant, 0.8% sodium casein (Sigma PN: C8654), and 5×TE. The resulting product is maintained at 56° C. until dry. Once dry, a mixture of 2.5% v/v of the rPA beads (prepared above) in a solution of 5% sucrose/2.5% trehalose/5×TE is prepared and sprayed onto the sample pad proximal to one end at 3 ul/mm using the Imagene Isoflow airbrush set to 4-5 psi at a height of 5-7 mm at a dispense rate of 75 mm/second. The labeled sample pads are dried overnight at 56° C., and stored in desiccated bags.

Example 5

Preparation of Strips

After baking, the Complex striped nitrocellulose cards are assembled into the test strips by adding the labeled protein A samples pads. This can be done by removing the release liner from the lower portion of the adhesive backed card proximal to the test line side containing the Complex, and firmly pressing the sample pad onto the adhesive area whereby 2 mm of the sample pad overhangs onto the striped nitrocellulose cards. An absorbent pad, such as Ahlstrom 222 is cut, the release liner removed from the adhesive card backing proximal to the reference line striped on the nitrocellulose, and pressed onto the adhesive backing whereby 2 mm of the absorbent pad overhangs the nitrocellulose membrane. The test card can now be cut into convenient size test strips, usually 4-5 mm depending upon the plastic cassette housings employed, using a Kinematic Matrix Model #2360 (Terra Haute, Calif.) guillotine cutter or equivalent.

Example 6

Assembly of Assay System

Test strips are placed into plastic cassette holders usually custom designed for the particular reader. The cut test strips are taken and placed in the lower portion of the cassette with the sample pad side at the bottom of the cassette. The top portion of the plastic housing is positioned over the test strip whereby the sample chamber is above the lower portion of the sample pad and the top is pressed into place. The assay is ready to use and can be stored and desiccated in polyfoil bags until needed at room temperature. Note also that a blood separation membrane may be employed above the sample pad to filter whole blood cells thereby conveniently allowing plasma to flow onto the pad. Separation membranes are commercially available, e.g. from Millipore, and are commonly used by those skilled in the art.

Example 7

Testing and Assay Usage

The clinical sample is brought to room temperature. The plastic housing containing the test strip is placed onto a flat surface at room temperature. After adding 75 ul (or other volume depending upon the width of the test strip) to the sample well, a timer is started, and the test results read at 30 minutes. If a visual test line can be seen anytime after about 5 minutes, the test is considered positive. The test results should not be read past 40 minutes because results will change due to sample evaporation.

What is claimed is:

1. A method of assisting in the diagnosis of heparin induced thrombocytopenia, in a patient, comprising quantitatively determining if a body fluid level of heparin-PF4 complex induced immunoglobulin antibodies in the patient is above a predetermined range using a point-of-care lateral flow immunoassay system, wherein the system comprises:
   a) a linear membrane of an inert, fibrous material capable of supporting movement of liquids by capillary flow, affixed to a supporting backing, wherein
      i) the membrane is zoned into a sample pad, a conjugate zone, a test line, a reference line, and a wicking pad, wherein each zone is separated from its adjacent zone by a flow zone,
      ii) protein A, which is affixed to an electromagnetic radiation absorbing or emitting label, is in the conjugate zone,
      iii) a heparin-platelet factor 4 complex is immobilized on the test line,
      iv) an antibody binding ligand capable of binding with the protein A is immobilized at the reference line, and
   b) a means for quantitatively measuring the electromagnetic radiation absorbed or emitted at the test line by the label affixed to protein A.

2. The method of claim 1 wherein the body fluid is blood or a component thereof.

3. The method of claim 1 wherein the immunoglobulin antibodies are IgG, IgA, IgE, or IgM antibodies.

4. A method of screening a patient for susceptibility to heparin induced thrombocytopenia comprising determining by means of a point-of-care lateral flow immunoassay system:
   a) if heparin-PF4 complex induced immunoglobulin antibodies are present in a body fluid of the patient, and
   b) if the antibodies are present in the body fluid, quantitatively determining the level of the antibodies
wherein the system comprises
   a) a linear membrane of an inert, fibrous material capable of supporting movement of liquids by capillary flow, affixed to a supporting backing, wherein
      i) the membrane is zoned into a sample pad, a conjugate zone, a test line, a reference line, and a wicking pad, wherein each zone is separated from its adjacent zone by a flow zone,
      ii) protein A, which is affixed to an electromagnetic radiation absorbing or emitting label, is in the conjugate zone,
      iii) a heparin-platelet factor 4 complex is immobilized on the test line,
      iv) an antibody binding ligand capable of binding with the protein A is immobilized at the reference line, and
   b) a means for quantitatively measuring the electromagnetic radiation absorbed or emitted at the test line by the label affixed to protein A.

5. The method of claim 4 wherein the body fluid is blood or a component thereof.

6. The method of claim 4 wherein the immunoglobulin antibodies are IgG, IgA, IgE, or IgM antibodies.

7. A method for assisting a physician in assessing a patient's vulnerability to heparin induced thrombocytopenia in a patient being administered heparin or a heparin containing medication comprising:
   a) determining a changing titer of heparin-PF4 complex induced immunoglobulin antibodies, judged by a physician to be indicative of a patient's vulnerability, or
   b) determining the rate of change of the titer of heparin-PF4 complex induced immunoglobulin antibodies as a function of time, judged by a physician to be indicative of a patient's vulnerability,
by making multiple assays of a body fluid level of heparin-PF4 complex induced immunoglobulin antibodies in the patient over a period of time using a rapid, cost effective, quantitative lateral flow immunoassay system, wherein the system comprises
   a) a linear membrane of an inert, fibrous material capable of supporting movement of liquids by capillary flow, affixed to a supporting backing, wherein
      i) the membrane is zoned into a sample pad, a conjugate zone, a test line, a reference line, and a wicking pad, wherein each zone is separated from its adjacent zone by a flow zone,
      ii) protein A, which is affixed to an electromagnetic radiation absorbing or emitting label, is in the conjugate zone,
      iii) a heparin-platelet factor 4 complex is immobilized on the test line,
      iv) an antibody binding ligand capable of binding with the protein A is immobilized at the reference line, and
   b) a means for quantitatively measuring the electromagnetic radiation absorbed or emitted at the test line by the label affixed to protein A.

8. The method claim 7 wherein the body fluid is blood or a component thereof.

9. The method of claim 7 wherein the immunoglobulin antibodies are IgG, IgA, IgE, or IgM antibodies.

10. A point-of-care lateral flow immunoassay system for quantitatively determining the body fluid level of heparin-platelet factor 4 complex induced immunoglobulin antibodies in a patient, wherein the system comprises:
    a) a linear membrane of an inert, fibrous material capable of supporting movement of liquids by capillary flow, affixed to a supporting backing, wherein
       i) the membrane is zoned into a sample pad, a conjugate zone, a test line, a reference line, and a wicking pad, wherein each zone is separated from its adjacent zone by a flow zone, ii) protein A, which is affixed to an electromagnetic radiation absorbing or emitting label, is in the conjugate zone, iii) a heparin-platelet factor 4 complex is immobilized on the test line, iv) an antibody binding ligand capable of binding with the protein A is immobilized at the reference line, and b) a means for quantitatively measuring the electromagnetic radiation absorbed or emitted at the test line by the label affixed to protein A.

11. The system of claim 10, wherein the body fluid is blood or a component thereof.

12. The system of claim 10, wherein the immunoglobulin antibodies are IgG, IgA, IgE, or IgM antibodies.

13. The system of claim 10 that uses electromagnetic radiation absorption, emission, or both of the label as detection means.

14. The system of claim 13 wherein electromagnetic detection means is fluorescence.

15. The system of claim 10 that uses biosensors in association with electronic circuitry as detection means.

16. The system of claim 15 wherein the biosensors are related to nanotechnology.

17. The system of claim 16 wherein nanotechnology is based on nanotube sensing.

18. The system of claim 10, wherein visibility of the antibodies is facilitated by an electro-optical reading device.

* * * * *